United States Patent
Plakas et al.

(10) Patent No.: US 11,419,492 B2
(45) Date of Patent: Aug. 23, 2022

(54) INTRAMEDULLARY CANNULATED GUIDE FOR FRACTURE REDUCTION WITH ENDOSCOPIC CAMERA

(71) Applicants: Dimitrios Plakas, Pylaia-Thessaloniki (GR); Christos Charalampidis, Salonika (GR)

(72) Inventors: Dimitrios Plakas, Pylaia-Thessaloniki (GR); Christos Charalampidis, Salonika (GR)

(73) Assignees: Georgios Perivolaris, Thessalonili (GR); Dimitrios Plakas; Christos Charalampidis

( * ) Notice: Subject to any disclaimer, the term of this patent is extended or adjusted under 35 U.S.C. 154(b) by 0 days.

(21) Appl. No.: 16/615,879

(22) PCT Filed: Nov. 17, 2017

(86) PCT No.: PCT/IB2017/057203
§ 371 (c)(1),
(2) Date: Nov. 22, 2019

(87) PCT Pub. No.: WO2018/122641
PCT Pub. Date: Jul. 5, 2018

(65) Prior Publication Data
US 2022/0015621 A1    Jan. 20, 2022

(30) Foreign Application Priority Data
Jun. 21, 2017  (GR) .............................. 20170100279

(51) Int. Cl.
*A61B 1/317* (2006.01)
*A61B 17/90* (2006.01)
(Continued)

(52) U.S. Cl.
CPC .............. *A61B 1/317* (2013.01); *A61B 1/005* (2013.01); *A61B 1/00105* (2013.01);
(Continued)

(58) Field of Classification Search
CPC ..... A61B 1/317; A61B 1/00105; A61B 1/005; A61B 1/015; A61B 1/053; A61B 1/06;
(Continued)

(56) References Cited

U.S. PATENT DOCUMENTS 7,237,556 B2 * 7/2007 Smothers ............... A61B 17/72
128/898
8,167,899 B2 * 5/2012 Justis .................. A61B 17/8819
606/184
(Continued)

FOREIGN PATENT DOCUMENTS

CN    102196778 A * 9/2011   ......... A61B 17/8836

*Primary Examiner* — Aaron B Fairchild

(57) ABSTRACT

The invention consists in a product for the closed reduction and, more specifically, in a new type of an intramedullary cannulated guide for fracture reduction with an endoscopic camera for use in intramedullary nailing surgeries. The intramedullary cannulated guide for fracture reduction is consisted of a flexible, unbreakable, modular and cannulated shaft, a T-handle with a hole in the upper surface, a camera, which is located at the edge of the guide, bears a lightning source and is connected wired or wireless to an image reproduction device, a sealing flange with a slot or spout, an input/output cannula for liquid suction and/or washing of the camera glass. The intramedullary cannulated guide for fracture reduction with an endoscopic camera is inserted in a bone that has suffered a fracture. The intramedullary image that the camera transmits, when it encounters the fracture point, is shown on the screen. Thus, the surgeon perceives the direction towards which the bone parts have to be pushed, in order to achieve their reduction with skeletal manipulations. After the intramedullary cannulated guide for
(Continued)

fracture reduction is inserted, the camera is removed from the guide, by pulling out the cable of the camera, and, through the canal of the guide, the ball tip guide wire is inserted and the surgery continues as it is conducted up until today.

8 Claims, 5 Drawing Sheets

(51) Int. Cl.
    *A61B 1/00*     (2006.01)
    *A61B 1/005*     (2006.01)
    *A61B 1/015*     (2006.01)
    *A61B 1/05*     (2006.01)
    *A61B 1/06*     (2006.01)
    *A61B 1/12*     (2006.01)

(52) U.S. Cl.
    CPC .............. *A61B 1/015* (2013.01); *A61B 1/053* (2013.01); *A61B 1/06* (2013.01); *A61B 1/126* (2013.01); *A61B 17/90* (2021.08)

(58) Field of Classification Search
    CPC ......... A61B 1/126; A61B 17/90; A61B 17/72; A61B 17/7208; A61B 17/8866; A61B 2017/90; A61B 34/20; A61B 90/361; A61B 2090/373; A61B 1/00135; A61B 1/00154
    See application file for complete search history.

(56) References Cited

U.S. PATENT DOCUMENTS

| | | | |
|---|---|---|---|
| 2003/0004513 A1* | 1/2003 | Guzman | A61B 1/00154 606/62 |
| 2012/0310248 A1* | 12/2012 | Govaers | A61B 17/15 606/87 |
| 2016/0066770 A1* | 3/2016 | Barbato | A61B 1/00144 600/138 |
| 2016/0089162 A1* | 3/2016 | Ardito | A61B 17/1764 606/98 |

* cited by examiner

INTRAMEDULLARY CANNULATED GUIDE FOR FRACTURE REDUCTION WITH ENDOSCOPIC CAMERA

The present invention concerns a product for the closed reduction of fractures and, more specifically, a new type of intramedullary cannulated guide for fracture reduction with an endoscopic camera for use in intramedullary nailing surgeries.

TECHNICAL FIELD

The reduction of long bones' fractures is made with four ways: by fitting a splint, with internal osteosynthesis, with external fixation and with intramedullary nailing (S. TERRY CANALE MD, JAMES H. BEATY MD. CAMPBELL'S OPERATIVE ORTHOPAEDICS, TWELFTH EDITION 2013 International Edition chapter's 53, 54, 55, 57).

The first intramedullary nailing surgeries have been recorded in the middle of the $18^{th}$ century. However, the founder of modern intramedullary nailing is considered to be Gerhard Kuentscher.

BACKGROUND ART

In today's intramedullary nailing practice, three informal stages are followed. First, a closed reduction of the fracture is made and a guide wire is inserted, then, the intramedullary nail is inserted and, finally, a distal locking of the intramedullary nail is made. These are the stages, as described in modern medical writings like "The Intramedullary Nailing" by Anastopoulos, (2011), Bong M R, Koval K J, Egol K A. The History of Intramedullary Nailing. Bulletin of the NYU Hospital for Joint Diseases. 2006; 64(3&4):94-97. Specifically, an entry point is being opened, through which a ball tip guide wire is being inserted in the bone, with the help of which the surgeon is trying to achieve the reduction, ie the alignment, of the bone parts, the near (central) part and the distal one, of the bone that has suffered a fracture, so that, subsequently, a cannulated nail can be inserted, which will eventually restrain the bone parts, in order to achieve the reduction of the fracture. The guide wire, which is compact in all of its length and not cannulated, is being inserted blindly in the bone parts. The nail is cannulated and is being inserted over the guide wire. The guide wire is then being removed and the stabilization of the nail follows. However, in order for the nail to be inserted, a reduction of the bone parts must be achieved first, meaning that the bone parts must be aligned along the sagittal and frontal axis, that is horizontally and vertically, so that the guide wire can be inserted first and, then, the reaming can take place, which will "rub" the internal cortex of the bone, so that the nail can, eventually, be inserted (el Moumni M, Leenhouts P A, ten Duis H J, Wendt K W: The incidence of non-union following undreamed intramedullary nailing of femoral shaft fractures, Injury 200940(2): 205-208, Giannoudis P V, Furlong A J, Macdonald D A, Smith R M: Reamed against undreamed nailing of the femoral diaphysis: a retrospective study of healing time. Injury 1997, 28(1): 15-18).

The reduction of the bone parts, which is the first stage of the surgery, is achieved with the use of a x-ray machine. More specifically, the patient, depending on the bone to which the intramedullary nailing is applied, is in a special position on an extension table, if the bone that suffered the fracture is the femur, and in an upright position on a surgical table, if the bone that suffered the fracture is the humerus or the tibia. The surgeon with his assistants, using an x-ray machine, is trying to achieve the reduction of the bone parts, that is to align them horizontally and vertically, so that the guide wire may enter and penetrate the two or more bone parts of the bone that suffered the fracture. That means that he takes intraoperative x-rays of the fracture, using the x-ray machine, so that he can perceive the position of the bone parts, and is trying to achieve their reduction manually, so that the guide wire can be inserted. This procedure is timely, as the x-ray machine takes shots using x-ray, i.e. it takes x-rays, which show the inner view of the limb as it was at the moment of the shot and not in real time. From the moment of the shot until the surgeon's and his assistants' next effort it is very likely that a bone part moves and, in this case, a new shot is needed from the x-ray machine. It should be noted that a bone fracture does not necessarily result in two bone parts, but the breakage may result in more than two bone parts that have to be rebuilt, that is to be aligned horizontally and vertically (comminuted fracture). Moreover, during the shots with the x-ray machine an upthrust, transverse and displacement of bone parts may be found, which results in that the x-ray shot taken from their side view (ML mediolateral) shows that the bone parts are aligned horizontally, while they are not aligned in their frontal view (AP anteroposterior) and vice versa, that is they may appear as aligned in the horizontal shot, but displaced in the vertical shot, resulting in that the bone parts would not be able to be rebuilt, so that they can be penetrated by the guide wire and, then, by the nail. The danger of upthrust, transverse and displacement of the bone parts imposes the taking of intraoperative x-rays both from the frontal view (AP anteroposterior) and the side view (ML mediolateral). Practically, this means that, between the two x-ray shots, from the frontal view (AP anteroposterior) and the side view (ML mediolateral), there is always a small movement of the patient or at least his limb that suffered the fracture. Thus, the surgeon must bring the limb that suffered the fracture within the shot frame of the x-ray machine for one shot from the frontal view (AP anteroposterior) and one shot from the side view (ML mediolateral), moving necessarily the limb that suffered the fracture as well as the x-ray machine. This essential movement often results in the movement of at least one bone part, this having as result that the previous shot taken by the x-ray machine becomes obsolete, as the position of the bone part, as it was imprinted in the previous shot, has changed. The result of this procedure is that tens or even hundreds of shots are taken until the reduction of the bone parts is achieved, that is until they are aligned horizontally and vertically.

The researches that have been conducted, up until today, focus mainly on the improvement of the composition of the material of the nail and the technique of its placement. In researches that have been made so far, many researchers dealt with the targeting of the distal screw with external target guide, in order to reduce the shots required to be taken by the x-ray machine and, as a result, to reduce the emitted radiation; Tyropoulos S, Garnavos C. A New Distal Targeting Device for Closed Interlocking Nailing. Injury. 2001; 32:732-735. U.S. Pat. No. 6,053,922 (1995) describes a cannulated reaming shaft, which is modular. The intramedullary cannulated guide with endoscopic camera is also modular. However, the shaft that is described in U.S. Pat. No. 6,053,922 does not bear a camera nor is it used for the closed reduction of fractures. The cannulated reaming shaft aims at the reaming, that is the "rubbing" of the bone canal, so that the cannulated nail can enter more easily and rebuild the fracture. The cannulated reaming shaft continues to be used after the present invention, as the invention does not influence that stage of the intramedullary nailing surgery nor does it try to replace the reaming guide wire or the reaming shaft.

The purpose of the invention is to find a solution in a problem that the orthopedic community faces in intramedullary nailing surgeries and, more specifically, in the closed reduction of fractures, that is in the first stage of the surgery.

In the techniques that are used, today, in intramedullary nailing, the closed reduction of fractures is one of the most difficult steps of the surgery. Difficult, timely and patient handling is required, along with a constant intraoperative x-ray control, so that a guide wire can be inserted from the central towards the distal part of the fractured bone. This particular medical act has been characterized as laborious, timely and as having a negative burden on the patient and on the personnel of the surgery due to the use of the x-ray control. It is often essential to have an extra incision and an access to the fracture area, so that the reduction of the fracture is made openly, in order for the guide wire to be inserted.

The basic and major problem in the closed reduction of fractures, in intramedullary nailing, is the use of a x-ray machine, which produces a very large quantity of radiation. On average, one hundred shots are taken per hour, while a surgery for the reduction of a fracture, using the method of intramedullary nailing, lasts from one and a half hour to several hours, depending on the shots that are needed to be taken, in order to achieve the reduction of the bone that suffered the fracture and the guide wire to be inserted, through which the nail will be installed. The shots are taken with x-ray both from the frontal view (AP anteroposterior) and from the side view (ML mediolateral) of the bone that suffered the fracture. The number of the shots required to be taken by the x-ray machine depends on the type of the fracture (spiral, oblique, transverse, bipolar, comminuted), as well as from the surgeon's and his assistants' skill to perceive the position of the bone parts during the shots, so that they move the bone parts, with skeletal manipulations, and achieve the reduction of the fracture. After every attempt to align the bone parts of the bone that suffered the fracture, new shots are taken from the frontal (AP anteroposterior) and the side view (ML mediolateral), in order to be ascertained whether the bone was rebuilt, that is if the bone has been aligned horizontally and vertically. The surgeon's and his assistants' attempt is conducted "blindly", resulting in the risk of injury to the soft tissues and noble elements around the fracture.

Moreover, a major problem is the quantity of radiation that the patient and the personnel receives. Indeed, the health professionals, often the patient himself, are shielded with x-ray lead apron, thyroid collars and retinal glasses. The use of a x-ray machine in such a degree is considered suspicious for carcinogenesis, leukemia and thyroid disorders (Barry T. P.: Radiation Exposure to an Orthopeadic Surgeon Clin Orthop.: 182: 160-164, 1984, National Research Council Committee on the Biologic effects of Ionizing Radiation: The Effects on Populations of Exposure to Low Levels of Ionizing Radiation: 1980, Washington D.C., National Academy of Sciences, 1980). Many hospitals grant days off, up to one month, to the personnel that participates in surgeries for fracture reduction with intramedullary nailing, so that their body drives away the accumulated radiation.

In addition to that, an important problem is the duration of the surgery, which can be up to several hours. The cost of such a surgery is also increased due to the use of the x-ray machine and shielding measures taken for protection against radiation.

DISCLOSURE OF INVENTION

The resolution of the above problems is achieved with the use of the intramedullary cannulated guide for fracture reduction that bears an endoscopic camera at its edge and has been sterilized, according to the general accepted rules of sterilization. The guide is intramedullary, which means that it is inserted through the canal of the bones. The intramedullary cannulated guide for fracture reduction consists of a flexible, break-proof, modular and cannulated shaft having length from 20 to 120 cm, internal diameter from 2 mm is to 9.5 mm, external diameter from 3 mm to 10.5 mm, a T-handle with a hole in the upper surface, a camera with a diameter from 1.5 mm to 8.5 mm, that is located at the edge of the guide, bears a lighting source and is connected with a wire or wireless to an image reproduction device, a sealing flange with a slot or spout, an input/output cannula for liquid suction and/or washing of the camera glass. The shaft of cannulated guide is radiant, at least at its edge (edge ring) and has graduated points measuring the length of the bone canal. The edge of the guide, at which the camera is located is blunt, smooth and non-traumatic, to prevent injury of the cortex of the bone. The fracture reduction guide is sterilized and his length is such as it is needed so that it can be used in long bones' fractures, that is in tibia, femur and humerus, in a way that, when the guide penetrates all the bone parts of the bone that suffered the fracture, a part of the guide remains outside of the entry point. The intramedullary cannulated guide, in the part that remains outside of the entry point, has a T-handle, which permits the user to handle the intramedullary cannulated guide for fracture reduction. The T-handle part is cannulated from the hole to flange. The camera passes through this canal. Moreover, on the part of the guide that remains outside of the entry point, the washing/suction cannulas and the sealing flange are located. The sealing flange is located at the point where the T-handle is connected with the shaft of the guide, at its transverse axis, so that there are no leaks either during the outflow of the blood or during the inflow of the washing fluid. The T-handle, the flange, the washing and/or suction cannulas, that the guide bears, are elements integrated to the T-handle of the cannulated guide for fracture reduction. The camera may be wired or wireless. The camera shaft, that is the cable, penetrates the canal of the intramedullary cannulated guide for fracture reduction and has such a length as needed in order for the camera, at the edge of its shaft, to reach the edge of the canal of the intramedullary cannulated guide for fracture reduction. After the reduction of the fracture is achieved, the camera is detached from the intramedullary cannulated guide for fracture reduction, by pulling out the cable, together with the camera. When the camera is wireless, it is still bind to a cable, which is used only for the pulling out of the camera. The power supply to the camera can be given with any known way of wired power supply or batteries. The diameter of the camera and of its shaft is 1 mm smaller compared to the internal diameter of the intramedullary cannulated guide for fracture reduction, so that there is a gap, which is used, on one hand, for the outflow of fluids and the inflow on washing fluid for the washing of the camera glass and, on the other hand, it facilitates the pulling out of the camera, after the fracture reduction has been achieved. After removing the camera, a ball tip guide wire is inserted through the intramedullary cannulated guide for fracture reduction, as conducted up until today. In particular, the intramedullary cannulated guide for fracture reduction, that is inserted through the entry point, bears at its edge the endoscopic camera, which is connected, wired or wireless, to an image reproduction device, that is located outside of the bone and to which the route of the intramedullary cannulated guide is displayed. The camera has a lighting source, in order to illuminate the area through which it passes. Moreover, as there is blood in the bone canal, the intramedullary cannulated guide for fracture reduction bears a washing mechanism, as well, in order to wash the glass of the camera. More specifically, it has two cannulas, under the T-handle, one on each side, one of which serves for the aspiration and outflow of fluids (blood) encountered by the intramedullary cannulated guide for fracture reduction during its passing through the canal of the bone, while the other one serves for the inflow of the washing fluid (sodium chloride solution). The washing fluid flows through the washing cannula, passes through the gap and in front of the glass of the camera. The camera is connected directly to an image reproduction device and transmits the image in real time or/and can be filming. The route of the guide is displayed on the screen. When the guide encounters the fracture area, the camera that is integrated to the guide enables the user to perceive, first of all, the transverse, the displacement, or the up thrust of the bone parts of the bone that suffered the fracture, while it enables him to perceive in real time the direction towards which the fractured bone part (distal bone part) has to be moved, in order to be aligned with the bone part through which the guide has been inserted (central bone part) and for the fracture reduction to be achieved. Thus, the time required and the handlings of the surgeon and/or his assistants are minimized, so that the reduction of the bone parts of the bone that suffered the fracture is achieved and the guide passes through them, without the use of an x-ray machine, without radiation and without shielding measures for the radiation. Subsequently, the guide wire can be inserted and the intramedullary cannulated guide for fracture reduction can be removed. After removing the intramedullary cannulated guide for fracture reduction, the intramedullary nail is inserted, at its place, over the guide wire. This means, that, after the reduction of the fractured bone parts has been achieved, the surgery can be continued as it was conducted before the invention of the intramedullary cannulated guide for fracture reduction.

The present invention resolves the above problems, as the minimization of use or even the abolishment of the x-ray machine is achieved, during the first stage of the surgery, that is during the closed reduction of the fracture and the insertion of the guide wire. Moreover, the minimization or even the abolishment of the shielding measures for the radiation is also achieved, while the duration of the surgery is reduced significantly, as the closed reduction of the fracture if the most timely stage. In addition to that, an important advantage of the invention is that enables the surgeon to work with great precision, it minimizes the possibilities for serious injury to soft tissues and noble elements around the fracture area, the loss of blood is minimal and manageable, as an additional incision of the skin and the muscles is avoided in order to access the fracture area, that involves diffusion of blood onto the surgical table, while the minimum contact of the personnel with patient's blood protects from infections and disease transmission. Finally, due to the accuracy of the surgery, the patient experiences minor post-surgery pains and recovers faster.

BRIEF DESCRIPTION OF DRAWINGS

The invention is described below, with the help of some examples and with reference to the accompanying drawings, in which the numbering is integral.

MODE(S) FOR CARRYING OUT THE INVENTION

In the first example (FIGS. 1-6), the intramedullary cannulated guide for fracture reduction with an endoscopic camera (2) is inserted, under obtuse angle, into a femur bone (17) that has suffered the fracture. The entry point (19) is approximately at the pelvis, while the fracture area (18) is approximately in the middle of the femur.

Figure 1:
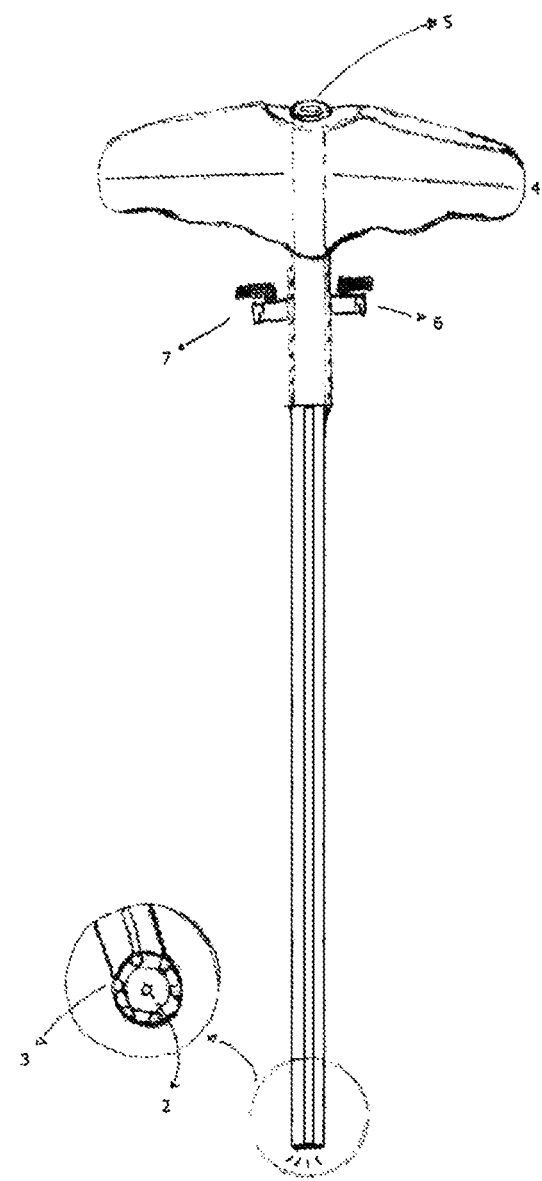
FIG. 1 shows the overall view of the intramedullary cannulated guide for fracture reduction, which consists of a flexible, unbreakable, modular cannulated shaft (1) having length from 20 cm to 120 cm, internal diameter from 2 mm to 9.5 mm, external diameter 3 mm to 10.5 mm, a camera with diameter from 1.5 mm to 8.5 mm (2) with a lighting source (3), a T-handle (4) with a hole hole on the upper surface (5), a washing cannula (6), a suction cannula (7). The part of the guide from the hole of the T-handle (5) to the camera (2) is cannulated.
Figure 2:
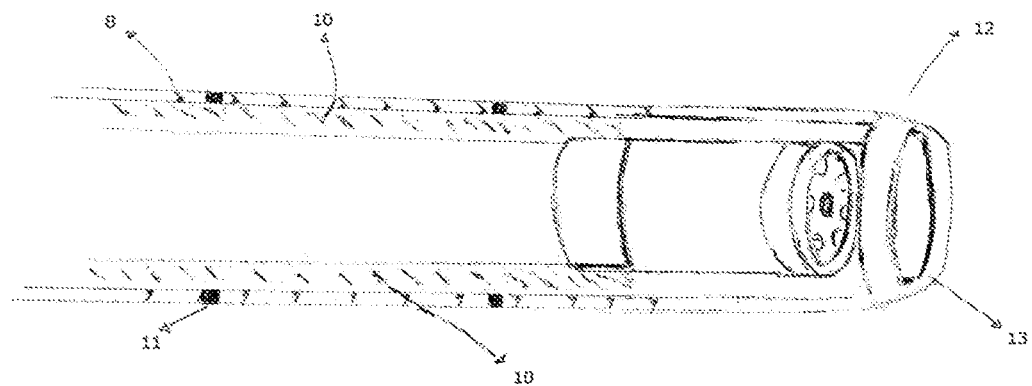
FIG. 2 shows the edge of the intramedullary cannulated guide for fracture reduction, the shaft of which is modular (8), meaning it consists of many small joints to make it more flexible. The shaft (the cable) of the camera (9) passes through the canal of the guide, while on the left and on the right of the camera shaft, there is a gap (10), through which, on one hand, the suction is made, i.e. the outflow of the fluids from the canal of the bone, and, on the other hand, the washing is made, i.e. the inflow of the washing fluids (sodium chloride solution). Moreover, the ring is shown (12) on the non-traumatic edge of the guide (13), which, at the minimum, is the part of the guide that is radiant.
Figure 3:
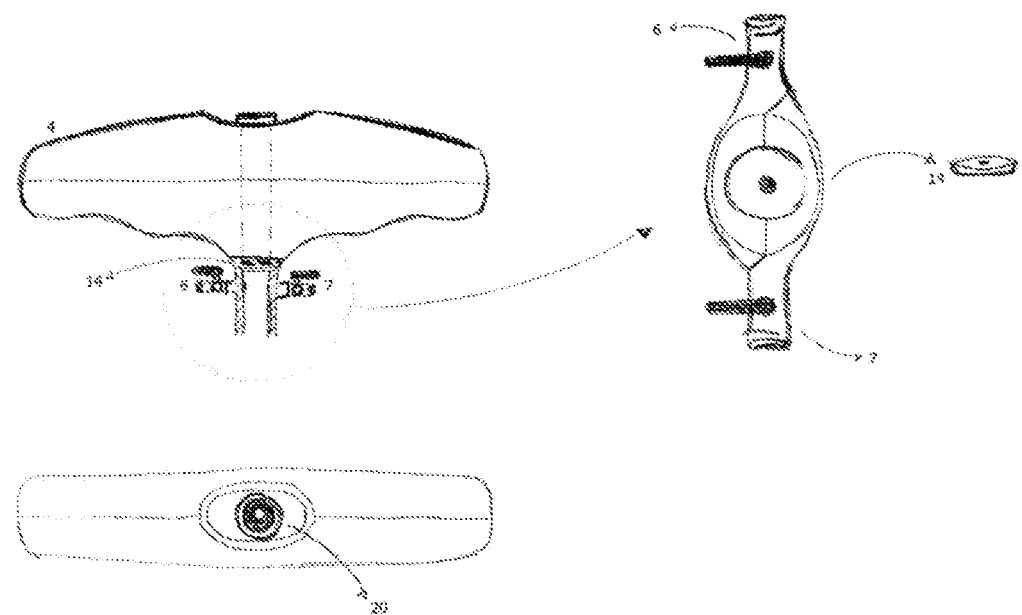
FIG. 3 shows the T-handle (4) from three points of view, that is from a side view, from a panoramic view and from a transverse-sectional view. In this figure the sealing flange is shown (14), which is located at the contact point of the T-handle with the shaft of the guide, slightly above from the washing (6) and suction (7) cannulas, while from the hole of the T-handle there is an exit of the wired connection to the image reproduction source (20).
Figure 4:
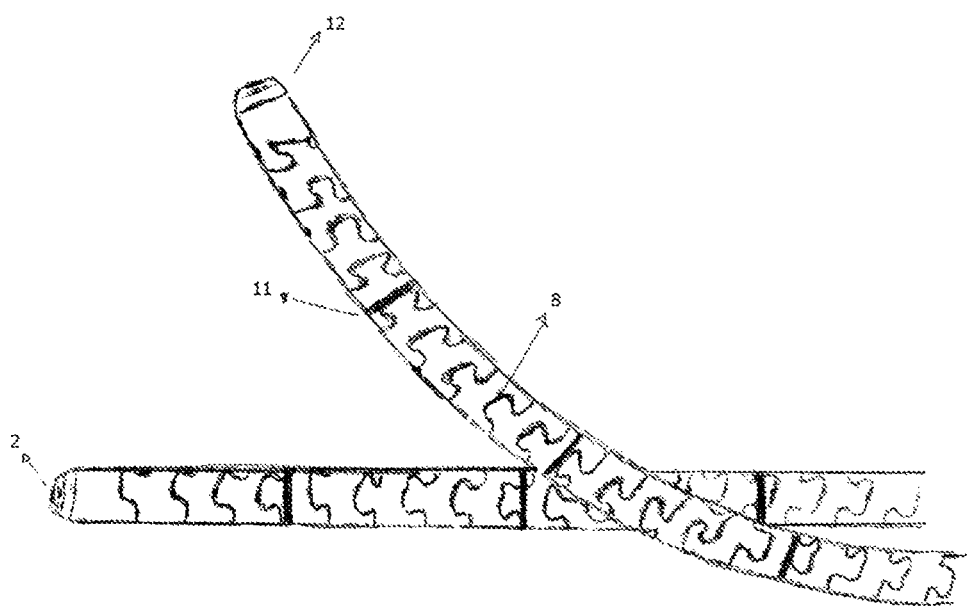
FIG. 4 shows the flexibility of the shaft of the guide, which is due to its joints (8). Moreover, there are graduated marks on the shaft for measuring the depth of the bone canal (11), while on the non-traumatic blunt edge (13), apart from the camera (2), there is a radiant marking ring (12). The entire shaft of the guide can be made from radiant material or, at least, the ring at its edge.
Figure 5:
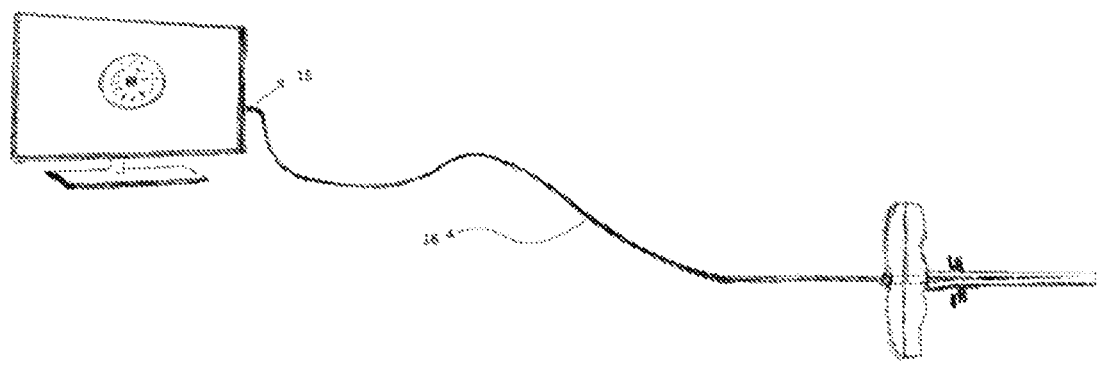
FIG. 5 illustrates the way that the camera is wirely connected to an image reproduction device (15) and the cable of the camera (16). The connection can be wireless, as well.
Figure 6:
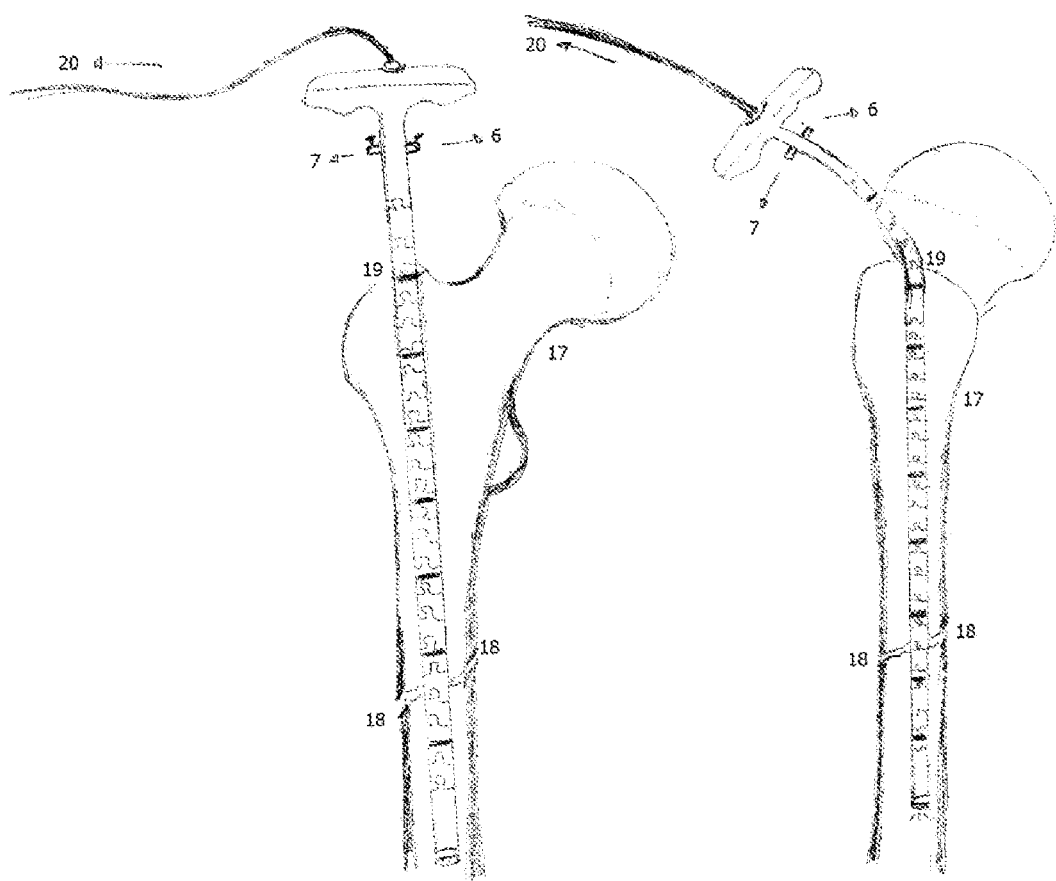
FIG. 6 shows the way the intramedullary cannulated guide is inserted into the bone (17) from the entry point (19), achieving the reduction of the bone parts of the fractured bone, penetrating the fracture area (18), while, simultaneously, the camera is wirely connected to an image reproduction device (20).
Figure 7:
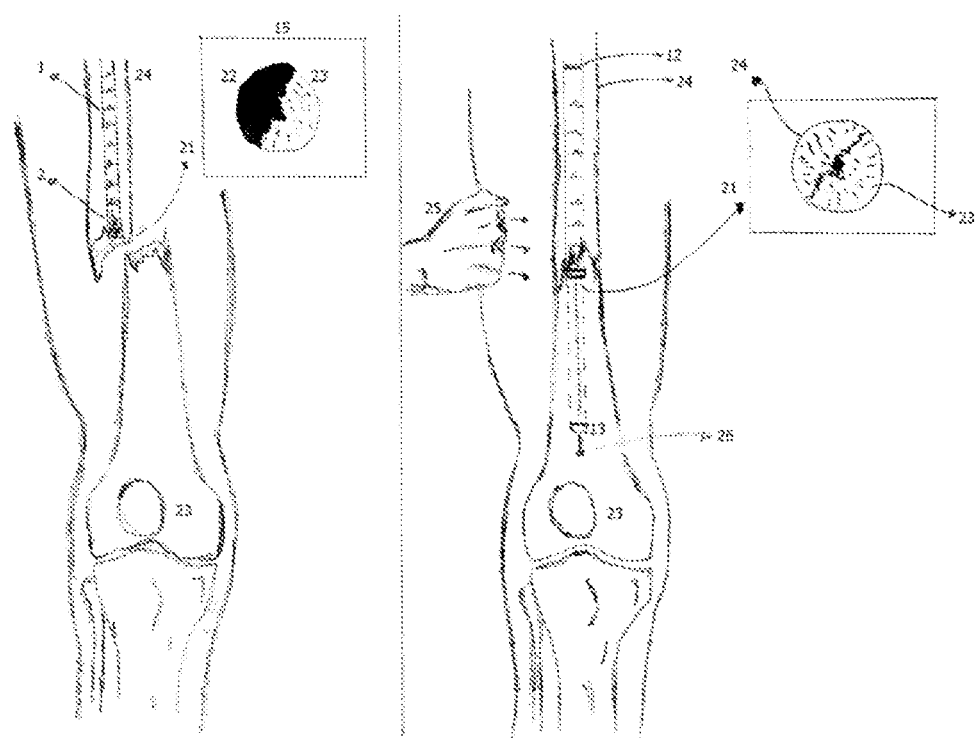
FIG. 7 shows the intramedullary image (21), i.e. the image from inside the canal of the bone, that the camera transmits (2) to the image reproduction device (15), in which the bone parts are displaced, the soft tissues are shown in black color (22). Moreover, the distal part of the bone is shown (23), i.e. the bone part that is more distant from the body, as well as the central part of the bone (24), i.e. the bone part that is closer to the body, both of which appear aligned, after the skeletal manipulations that lead to the fracture reduction to be achieved (25). After the reduction of the bone parts is achieved, the ball tip guide wire (26) passes through the intramedullary cannulated guide.

In the second example (FIG. 7), the intramedullary cannulated guide for fracture reduction with an endoscopic camera (2) is inserted, into a bone (17) that has suffered a fracture. On the screen (15) the image in the inner of the canal is shown (21) as taken from the camera, when it encounters the fracture area, where the soft tissues (22) are shown in black color, while the distal bone part in white color (23). Thus, the surgeon perceives the direction towards which the bone parts have to be pushed, in order to achieve their reduction with skeletal manipulations (25). As soon as their reduction is achieved, the image in the inner of the canal (21) as shown on the screen is diversified and shows the distal part of the bone (23) and the central part of the bone (24) to complete each other, while there is no black color any more, i.e. soft tissues, that suggest a transverse, up thrust or displacement of the bone parts. After the fracture reduction, the intramedullary cannulated guide for fracture reduction with an endoscopic camera passes through the distal part of the bone (23). After the reduction of the fractured bone, the camera is removed from the guide, by pulling out the cable of the camera, and the ball tip guide wire (26) is inserted, through the canal of the guide and the surgery continues as it is conducted up until today.

The invention claimed is:

1. A method for achieving fracture reduction in long bones, comprising:
   inserting a cannulated guide into a bone canal, where the guide comprises a T-handle and a flexible shaft,
   passing a wired camera and a lighting source through the guide and stopping them at an edge of the guide,
   viewing a fracture in a long bone having the bone canal on a monitor, to which the camera is connected, in real time;
   the surgeon manually aligning parts of the fractured long bone based on the real time monitoring of the fracture;
   removing the wired camera and replacing the wired camera with a ball tip guide wire;
   removing the ball tip guide wire;
   and placing a nail through the guide.

2. The method for achieving fracture reduction in long bones of claim 1, further wherein:
   the shaft is cannulated, has a length in the range of 20 to 120 centimeters, has an internal diameter from 2 to 9.5 millimeters, and has an external diameter from 3 to 10.5 millimeters;
   the wired camera has diameter from 1.5 to 8.5 millimeters.

3. The method for achieving fracture reduction in long bones of claim 2, further wherein:
   the wired camera is detachable.

4. The method for achieving fracture reduction in long bones of claim 2, further wherein:
   the shaft is modular.

5. The method for achieving fracture reduction in long bones of claim 2, further wherein:
   the tip of the guide is blunt and smooth.

6. The method for achieving fracture reduction in long bones of claim 2, further wherein:
   the shaft bears graduated points for measuring the length of the bone canal.

7. The method for achieving fracture reduction in long bones of claim 2, further wherein:
   there is an output fluid spout, at a point where the T-handle and the shaft meet, through which the fluids that the intramedullary cannulated guide for fracture reduction encounters, during its passing through in the bone canal, are being sucked out and outflow.

8. The method for achieving fracture reduction in long bones of claim 2, further wherein:
   there is an input fluid spout, at the point where the T-handle and the shaft meet, through which a washing fluid passes for washing a glass of a camera.

\* \* \* \* \*